(12) United States Patent
Ukraintsev et al.

(10) Patent No.: US 10,175,295 B2
(45) Date of Patent: Jan. 8, 2019

(54) OPTICAL NANOPROBING OF INTEGRATED CIRCUITS

(71) Applicant: FEI Company, Hillsboro, OR (US)

(72) Inventors: Vladimir A. Ukraintsev, Allen, TX (US); Mike Berkmyre, Princeton, TX (US)

(73) Assignee: FEI COMPANY, Hillsboro, OR (US)

( * ) Notice: Subject to any disclaimer, the term of this patent is extended or adjusted under 35 U.S.C. 154(b) by 378 days.

(21) Appl. No.: 15/192,976

(22) Filed: Jun. 24, 2016

(65) Prior Publication Data

US 2016/0377675 A1     Dec. 29, 2016

Related U.S. Application Data

(60) Provisional application No. 62/184,822, filed on Jun. 25, 2015.

(51) Int. Cl.
    *G01N 21/65*        (2006.01)
    *G01R 31/311*      (2006.01)

(52) U.S. Cl.
    CPC .......... *G01R 31/311* (2013.01); *G01N 21/658* (2013.01); *Y10S 977/901* (2013.01)

(58) Field of Classification Search
    CPC .. G01N 21/658; G01R 31/311; Y10S 977/901
    See application file for complete search history.

(56) References Cited

U.S. PATENT DOCUMENTS

| 2011/0055984 A1* | 3/2011 | Cheng | B82Y 20/00 |
| --- | --- | --- | --- |
| | | | 850/32 |
| 2014/0259234 A1* | 9/2014 | Raschke | G01Q 10/00 |
| | | | 850/1 |
| 2015/0377958 A1* | 12/2015 | Ukraintsev | G01Q 30/02 |
| | | | 324/750.18 |

\* cited by examiner

*Primary Examiner* — Mark R Gaworecki
(74) *Attorney, Agent, or Firm* — Denton W. McAlister

(57) ABSTRACT

Apparatus for electrical and optical nanoprobing at resolution beyond optical diffraction limit. Navigation microscope is configured for navigation to a region of interest. A probe spatial positioner supports a fork and an oscillating piezotube is attached to the free end of the fork and provides an output indicating of a distance to the sample. A single-mode optical fiber having a near-field transducer formed at an end thereof is attached to the oscillating piezotube such that the near-field transducer extends below the oscillating piezotube towards the sample. A photodetector is positioned to detect photons collected from the sample. The near-field transducer may be formed as a tapered section formed at the end of the single-mode optical fiber, a metallic coating formed at a tip of the tapered section, and an aperture formed in the metallic coating so as to expose the tip of the tapered section through the metallic coating.

33 Claims, 10 Drawing Sheets

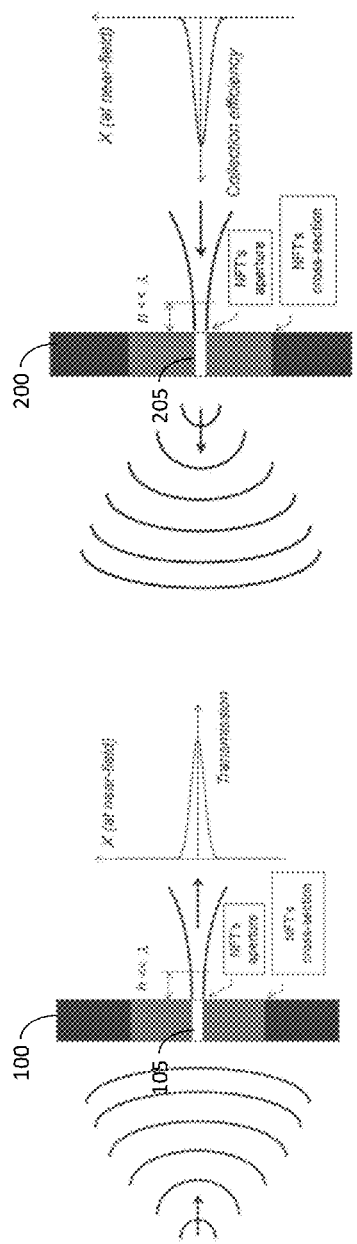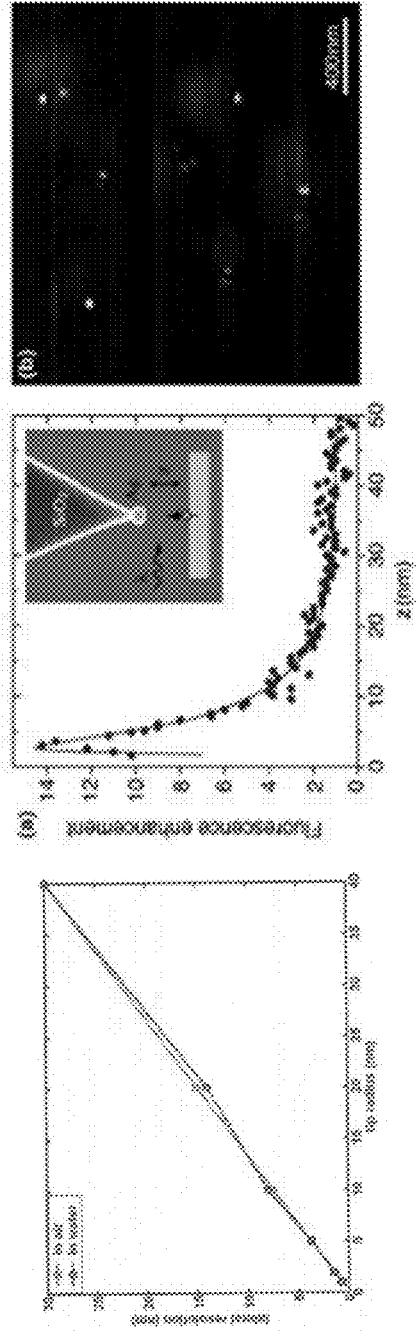
Figure 1
Figure 2
Figure 3
Figure 4A
Figure 4B

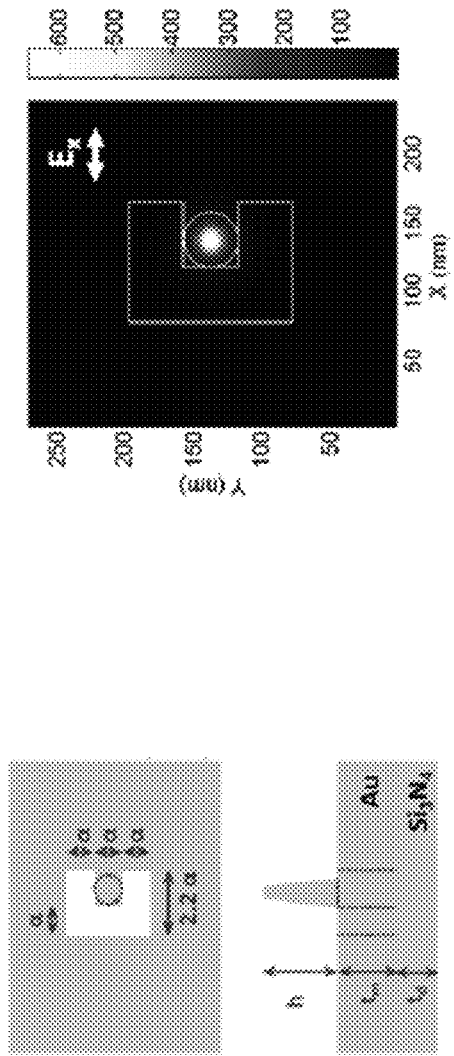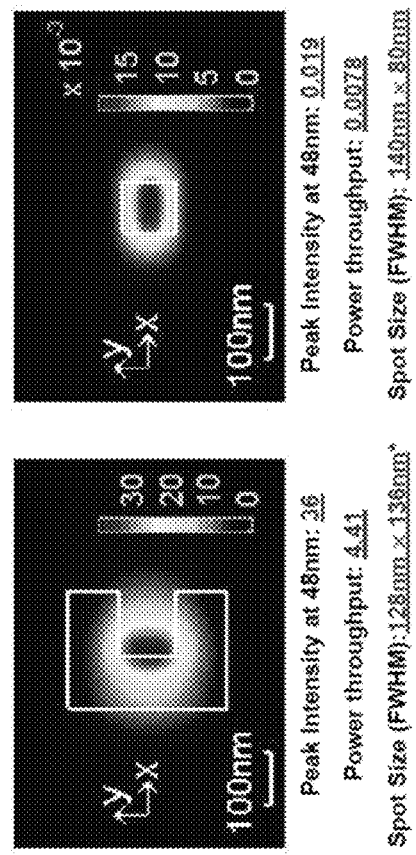

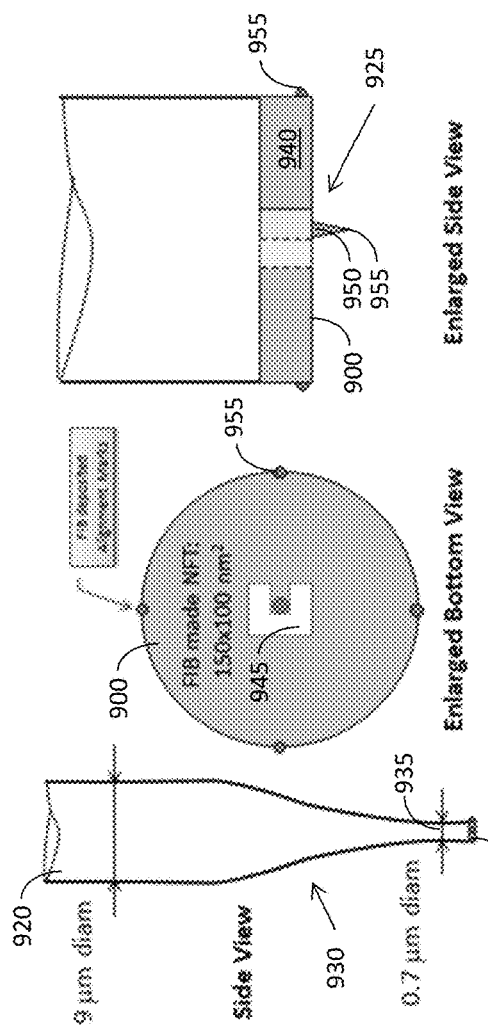
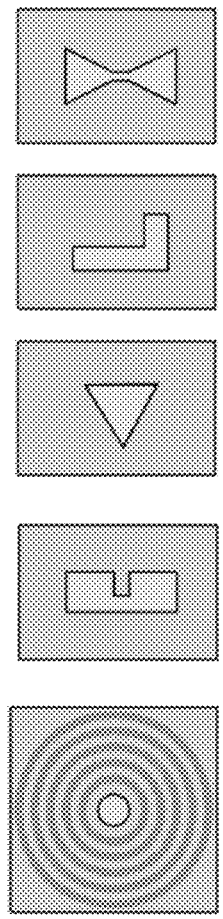
Figure 9

OPTICAL NANOPROBING OF INTEGRATED CIRCUITS

CROSS-REFERENCE TO RELATED APPLICATIONS

This application claims priority benefit from U.S. Provisional Patent Application, Ser. No. 62/184,822, filed on Jun. 25, 2015, the entire content of which is incorporated herein by reference.

BACKGROUND

1. Field of Invention

This invention is in the field of optoelectrical characterization of integrated circuits (IC) using scanning or/and stepping (touching) nanoprobing systems.

2. Related Art

Nanoprobing covers a broad field of analytical science including various types of dimensional, electrical, mechanical, compositional and chemical physical characterization of nanoobjects. Nanoelectronic devices, such as advanced (<130 nm) ICs, are examples of such objects.

Conventional far-field optical probing, which uses 1000-1500 nm laser, is running out of resolution. Currently even the most sophisticated photon delivery and collection optics (solid immersion lens SIL) provides lateral resolution of about 200 nm and with some even greater efforts about 100 nm. Required spatial resolution of optics is about twice of the minimum gate (or contact level) pitch. The pitch dimension of transistors at technology nodes is about 140 nm for the 20 nm node, 100 nm for the 14 nm node, 70 nm for the 10 nm node and 50 nm for the 7 nm node; these dimensions are also the requirements for the resolution of optical probing of transistors. Therefore, resolution of optical commercial/industrial probers must be improved to follow Moore's Law—the industry trend.

Near-field scanning optical microscopy (NSOM) is a known way of improving resolution of optics beyond the diffraction limit. This solution has a serious limitation related to strong dependence of photon collection efficiency on the ratio of aperture diameter to wavelength (a fourth power dependence by Bethe's theory). For 1250 nm unpolarized photons (the middle of 1000 nm to 1500 nm range currently used by optical circuit analysis) and 200 nm aperture diameter, efficiency is close to 1.5%, for 50 nm aperture it is only 0.006%. At most only one of 17,000 photons emitted by sample is collected. For practical applications photon collection efficiency is inadequate.

To overcome diffraction limits of optical microscopy resolution, various near-field evanescence radiation approaches were used in the past. Example: NSOM which uses fiber opening with dimensions less than the diffraction limit. In the near-field case, resolution of the system is defined by the aperture of optical probe (fiber, pin hole, etc.). The problem with any near-field evanescence method is its poor photon delivery and collection efficiency. Collection efficiency of NSOM with fiber probes is falling with diameter of the fiber aperture or with its spatial resolution as $D^3$ (experiment) or even $D^4$ (theory) function. For 1250 nm light expected transmission of 100 nm pin hole is about 0.0001 and for 50 nm resolution one should expect 0.00006 transmissions. This even further reduces the method's throughput and makes fiber NSOM-based high-resolution optical circuit analysis (OCA) simply impractical.

The goal is to collect every possible photon interacted with or emitted by the targeted transistor/diode and yet to preserve required spatial resolution. The near-field transducers (NFT) or/and optical nano-antennas have been used to concentrate optical energy in spot size less than the diffraction limit. This recent NFT development is supported by data storage companies because the heat assisted magnetic recording (HAMR) technology promises to achieve higher densities of data storage. Resolution of ~20 nm in near-field can be achieved today using various NFT's with transmission at 800 nm wavelength (or coupling with magnetic media efficiency) from a few to tens of percent. Note the wavelengths needed with NSOM for optical probing can be shorter than for far field probing; however, far field probing can work with silicon thicknesses of more than 10 um, whereas NSOM must work with silicon thicknesses of less than 250 nm. These numbers should be compared with transmission of simple metal aperture of 20 nm in diameter which is about 0.0002%. Therefore, NFT's significantly improve efficiency (transmission, coupling efficiency) of near-field optics.

The spatial resolution of an imaging far-field optical system used to collect photons from multiple points of the region of interest (ROI) with a laser scanning system is limited fundamentally by what is called the diffraction limit, defined by Ernest Abbe. This spatial resolution depends on wavelength, numerical aperture as well as quality of optical system and emission, reflection or absorption properties of the sample. This same diffraction limit restricts the reduction of a laser probe below a certain size. This limit is again defined by wavelength, numerical aperture and quality of focusing optics. A few techniques are known which help to overcome the diffraction limit to resolution of an optical system. One of them is scanning or positioning a nanoscale photon sensor/source in the near-field of the ROI. NSOM in which an aperture of conductor coated optical fiber defines the "sensor/source" size can be used. Despite poor transmission of a thin fiber, this type of NSOM is sometimes employed to deliver photons to a ROI with a nanoscale resolution (high power of a source laser helps). However, use of NSOM for collection of emitted or reflected photons is limited. Theoretical photon collection efficiency of sub-wavelength aperture drops as the fourth power of diameter to wavelength ratio. Some experimental data suggests slightly less abrupt decay of etched and metal coated fiber transmission—as the third power of diameter to wavelength ratio. Even in this third power case going from 250 nm resolution provided by far-field optics to 50 nm resolution of NSOM will cause signal reduction of more than 2 orders of magnitude (1/125 or 0.008). Considering sequential data collection algorithms of NSOM one faces a significant loss of throughput going from parallel imaging with 250 nm resolution to sequential scanning microscopy with 50 nm resolution (only extra data collection time can improve the signal-to-noise ratio, SNR). Photon collection efficiency (or transmission) of the nanoscale, sub-wavelength optics must be significantly improved for the method to be accepted for industrial applications.

Accordingly, there is a need in the art to enable probing of IC's at the upcoming design nodes, which cannot be probed using current technology due to insufficient resolution and/or photon collection efficiency. This disclosure describes the system and method for doing that.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Disclosed embodiments achieve nanoscale spatial resolution of optical probing by utilizing an NFT incorporated with a scanning or stepping nanoprobing system. Spatial resolution of this (mechanically) scanning optical system is defined by the size of optical probe in the near-field scanning optical microscope (NSOM).

According to disclosed embodiments, near-field transducers technology developed for HAMR can be applied to OCA techniques based on local heating/irradiation of elements of working IC. For examples, Dynamic Thermal Laser Stimulation and Static Thermal Laser Stimulation, in which the wavelength must be higher than 1250 nm may be implemented using these embodiments. In the disclosed embodiments, the HAMR NFT's are designed to be placed at a few tens of nanometer distance (15 to 25 nm) from the target to operate properly—much reduced distance than typical NSOMs.

Aspects of the invention include, but are not limited to, a scanning or stepping prober with nano-size optical probe used to deliver to or collect photons from energized IC with nanoscale spatial resolution (a single NFT or a combination of more than one NFT to be used for high efficiency photon collection and delivery). A microscope (optical or scanning electron or scanning ion or any other) may be used for navigation on the sample to the ROI. The inventive integrated nanosensor combines NFT(s) and photon sensor, or uses fiber optics or far-field optics (lens) to couple NFT(s) and photon sensor. Alternatively, an integrated nanosource combines NFT(s) and source of photons directly or using fiber optics or far-field optics (lens) to couple NFT(s) and the photon source. The nanosensor or nanosource may be glued to a piezo tube, which is used for maintaining a specified angle and distance between the NFT and the sample surface. The oscillating piezo tube is also used to detect surface touch and/or proximity during probe landing. This is done through monitoring of dampening of probe oscillation (amplitude and/or phase). In some embodiments, photon delivery to or collection from the sample is done using far-field optics focused on the ROI, simultaneously with near-field optics used for collection or delivery of photons, respectively.

According to other aspects, a method of performing electrical and optical sample nanoprobing with resolution beyond optical diffraction limit is enabled, including the steps of: thinning or delayering of IC to bring probing elements in near-field proximity (e.g., less than 1/10 wavelength) with NFT; navigating to the ROI using microscope (optical or scanning electron or scanning ion or any other); scanning/stepping optical nanoscale inspection (photon emission/scattering) of energized circuit under test or use of nanoscale source of photons to disturb circuit under test (SLS: OBIRCH, TIVA, OBIC, LIVA, Seeback effect, etc.); implementation of backside and frontside optical probing using functional tester or electrical probes to energize IC from frontside; use of time-resolved electro-optical methods (pulsing) to detect and characterize soft failures (SDL, LADA, CPA, SIFT); localize and characterize soft and hard failed elements of IC.

Aspects of the invention further include the following features: use of high transmission NFT (single or combination of more than one NFT) in OCA with resolution below diffraction limit; use of 3D nano motion transducer (example: piezo tube) to improve NFT's collection efficiency through optimizing angle and distance between the NFT and the sample surface; and, employment of efficient NFT's for fast high-resolution analysis of devices and circuits in frontside and backside nanoprobing.

According to disclosed embodiments, a method of probing a sample in a probing system using an NFT integrated with a nanoprober is provided, comprising: affixing a sample to a stage; affixing a single mode fiber optic, having an NFT formed at its sampling tip, to a piezo tube, wherein the piezo tube is attached to a fork of a nanoprober; using the stage to register a region of interest (ROI) of the sample to coordinates of the probing system; energizing a positioner of the nanoprober to bring NFT to within a prescribed distance from top surface of the ROI, wherein the prescribed distance comprises near-field proximity, near-field proximity being a fraction, e.g., one-tenth, of the wavelength used during the probing; determining proximity of the NFT to the top surface by monitoring the dampening of the piezo tube; scanning the NFT over the top surface of the ROI.

According to aspects of the invention, a method for fabricating a near-field transducer for operating at preselected wavelength is provided, comprising: providing a single mode fiber having a diameter larger than the wavelength; forming a thinned section at one end of the single mode fiber, wherein the thinned section terminates at a flat bottom having a diameter that is smaller than the wavelengths; coating the flat bottom with an opaque layer; cutting an aperture in the opaque layer, the aperture having dimensions optimized for the preselected wavelengths and being smaller than the preselected wavelengths; growing a metal tip on the opaque layer in the vicinity of the aperture; and, forming alignment marks on an outer perimeter of the opaque layer. The opaque layer may be made of metal, such as, e.g., gold. The aperture may be formed to have a C shape and the metal tip can be formed at the center of the C shape aperture. The tip can be grown to have a height of from 50 to 100 nm and may be grown using focused ion beam assisted chemical vapor deposition. The alignment marks may be metallic bumps grown using focused ion beam or are etched onto the opaque layer using focused ion beam.

Aspect of the invention provide a prober integrating a near-field transducer, comprising: a probe spatial positioner; a fork attached to the positioner; an oscillating piezotube attached to a free end of the fork; electrical leads attached to the oscillating piezotube; an optical fiber having a near-field transducer formed at an end thereof, the optical fiber being attached to the oscillating piezotube such that the near-field transducer extends below the oscillating piezotube; wherein the near-field transducer comprises a tapered section formed at the end of the optical fiber, a metallic coating formed at a tip of the tapered section, and an aperture formed in the metallic coating so as to expose the tip of the tapered section through the metallic coating. The near-field transducer may further comprise a metal tip extending from the metallic coating, extending to a height of from 50 nm to 100 nm and has a tip apex of diameter of from 20 nm to 30 nm.

Aspect of the invention also provide an apparatus for performing electrical and optical sample nanoprobing with resolution beyond optical diffraction limit, comprising: a sample holder; a navigation microscope configured for navigation over the sample to a region of interest (ROI); a probe spatial positioner; a fork attached to the positioner; an oscillating piezotube attached to a free end of the fork and providing an output indicating of a distance to the sample; electrical leads attached to the oscillating piezotube; a single-mode optical fiber having a near-field transducer formed at an end thereof, the optical fiber being attached to the oscillating piezotube such that the near-field transducer extends below the oscillating piezotube towards the sample; a photodetector; wherein the near-field transducer comprises a tapered section formed at the end of the single-mode optical fiber, a metallic coating formed at a tip of the tapered section, and an aperture formed in the metallic coating so as to expose the tip of the tapered section through the metallic coating. The apparatus may further comprise: a laser positioned to provide a laser beam into the single-mode optical fiber; a collection objective positioned to collect light reflected from the sample and direct the reflected light onto the photodetector; and a polarizer positioned between the collecting objective and the photodetector. The apparatus may further comprise: a laser positioned to provide a laser beam towards the sample; an objective positioned to focus the laser beam from the laser source onto the ROI; a polarizer positioned at an exit side of the single-mode optical fiber; wherein the photodetector is positioned behind the polarizer and receives light passing through the polarizer. The apparatus may further comprise a plurality of conductive nanoprobes attached to the positioner and electrically coupled to a signal source.

According to aspects of the invention, many devices energized simultaneously and even large circuits can be characterized with high spatial resolution using a single or more than one near-field nanosensor.

According to another aspect a capability to deliver photons to the energized circuit with high spatial resolution is enabled.

BRIEF DESCRIPTION OF THE DRAWINGS

Other aspects and features of the invention would be apparent from the detailed description, which is made with reference to the following drawings. It should be mentioned that the detailed description and the drawings provide various non-limiting examples of various embodiments of the invention, which is defined by the appended claims.

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1 is an illustration of sub-wavelength focusing of light using NFT according to one embodiment.

FIG. 2 is an illustration of photon collection from sub-wavelength sources of light using NFT according to one embodiment.

FIG. 3 is a plot Lateral resolution of scattered electric field or full-width-at-half-maximum of (electric field)$^4$ as function of tip radius, for gold tip in air and water.

FIGS. 4A and 4B illustrate enhancement of the radiation rate of a single molecule with a silver nanoparticle antenna according to a disclosed embodiment.

FIG. 5A is a schematic of the CAN-Tip, while FIG. 5B is a plot of the near-field profile as calculated for 980 nm light at 6 nm from the tip of a CAN-Tip.

FIGS. 6A and 6B compare transmission and peak light intensity of C-aperture with characteristic size a=100 nm and square aperture of 100 nm size.

FIG. 9 shows an embodiment of integration of NFT with optical fiber, according to one embodiment.

FIGS. 9A-9E illustrate various embodiments for the NFT cavity of the optical fiber.

DETAILED DESCRIPTION

Figure 7:
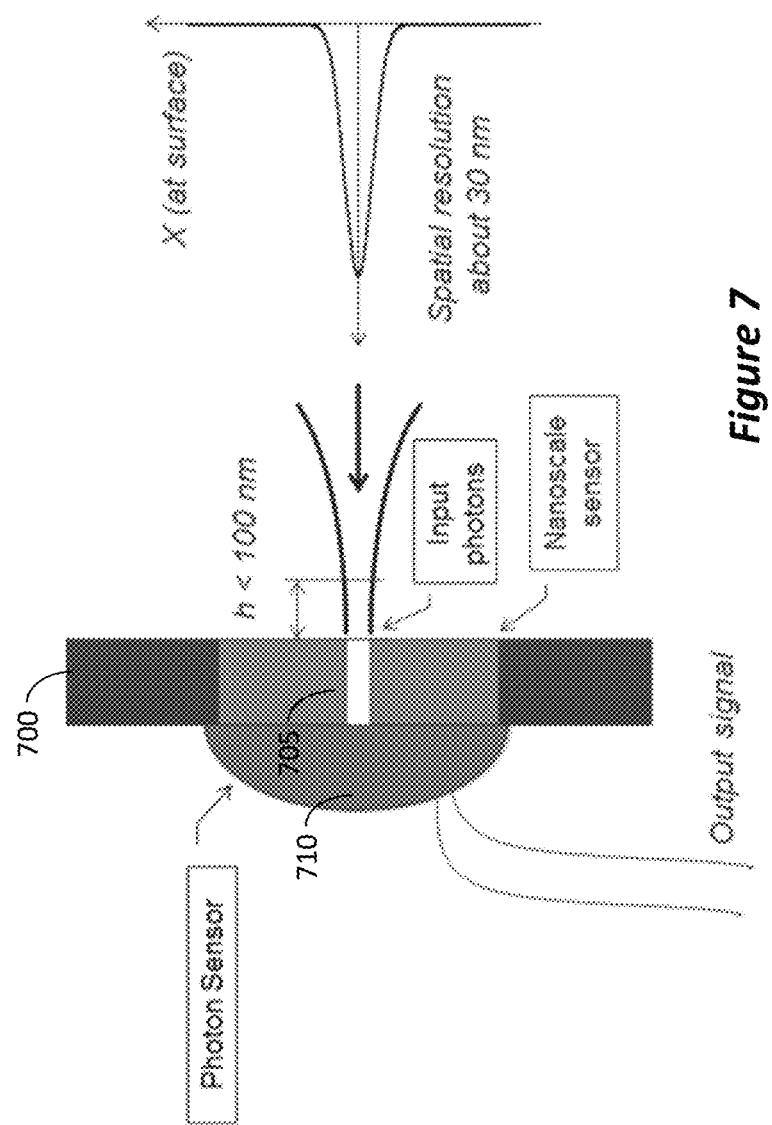
FIG. 7 is a schematic of an embodiment for integration of NFT and photosensor.

Relatively little is known about photon collection using NFT's. FIGS. 1 and 2 present illustrations of principals of both processes: photon delivery to the sample and collection of photons emitted by the sample, as implemented in disclosed embodiments.

FIG. 1 is an illustration of sub-wavelength focusing of light using NFT. Focused or plane wave (shown on the left) diffracts on plasmonic NFT 100 with effective cross-section of a few hundreds of nanometers. Intensified light penetrates to the right semi space through NFT's aperture 105, which defines dimensions of the focused beam in the near-field, wherein the aperture diameter is much smaller than the illumination wavelength and the object to be imaged is located a subwavelength distance from the aperture (h<<$\lambda$). Coupling efficiency or transmission of tens of percent can be achieved with NFT's. Light intensity of the focused beam may significantly (more than 100×) exceed the incident light intensity.

FIG. 2 is an illustration of photon collection from sub-wavelength sources of light using NFT. Photons emitted by sub-wavelength source (right) are collected by plasmonic NFT 200 with effective cross-section of a few hundreds of nanometers. Maximum collection efficiency of NFT of tens of percent is expected. Collection efficiency drops fast with aperture-source misalignment. That provides high, nanometer, spatial resolution of NFT-based photon collection system. To achieve high resolution and collection efficiency the light source has to be placed at the near-field distance (h<<$\lambda$) from the NFT. Far- or near-field detector can be used to count photons transmitted to the left semi space.

As follows from FIGS. 1 and 2, NFT improves spatial resolution and also sensitivity or signal to noise ratio of conventional optical circuit analysis, since electro-magnetic field (EM) is enhanced through re-distribution of photons in the proximity of the NFT. The transducer "funnel" or "antenna" analogy can be used to comprehend how this redistribution works. EM field and density of incoming photons are amplified in the gap between NFT and sample by more than two orders of magnitude (FIG. 1). For emitted or/and scattered photons (FIG. 2) collected using NFT the inverse path must be considered. Photon's collection probability (photon transfer function of the NFT) is higher in the nanometer proximity of the NFT to the source of the photons (and can be up to tens of percent). Therefore, once the NFT is placed over the targeted emitting/scattering active element, the signal increases indicating its origin at (X,Y) with NFT's spatial resolution. That is, the drastic drop in collection efficiency due to misalignment of the NFT and the target can be used to accurately determine the spatial location of the emitting element, using the available accuracy of the placement of the NFT. Compare this process with collection of photons using fiber NSOM probe, where emitted photons are mostly scattered/reflected back by the fiber tip and only a few of them enter the fiber through the sub-wavelength aperture.

At this point no non-linear processes are considered to enhance lateral resolution of optical probing. However, SHSG (second harmonic surface generation), Raman and fluorescence scattering can be used to improve lateral resolution even further since intensity of generated second harmonic or Raman or fluorescence photons is proportional to fourth power of electric field of incident photons. Assuming ~$10^2$ enhancement of electrical field near NFT's aperture, one should expect ~$10^8$ enhancement of SHSG or Raman yield. This effect is used in so-called tip-enhanced Raman spectroscopy (TERS).

Simulations were performed of electrical field (E) around isolated gold tip of radius 1 nm. The surrounding media is air, and the tip is illuminated with p-polarized light of wavelength 886 nm and at 45 degrees. The spectral dependence of the enhancement of the electric field E at the tip apex, for gold tips of various radii were plotted. Values of scattered electric field were also plotted. The overall optical enhancement of scattered electric field was showed to be up to about 108, i.e., enough for near-field signal to dominate over the far-field signal. The simulations predict significant (~$10^2$) EM field enhancement under nanometer size metal tip approaching metal or dielectric sample. In this case metal nanoparticle (tip apex) is used as a NFT. The EM enhancement should lead to $10^8$ gain in yield of scattered photons (Raman, fluorescence, second harmonic, etc.) and significant improvement in lateral resolution of optical spectroscopy and SHSG.

FIG. 3 is a plot of a lateral resolution of scattered electric field or full-width-at-half-maximum of (electric field)$^4$ as function of tip radius, for gold tip in air and water. The slope is 0.75, meaning that resolution is about 0.75 of the tip radius.

This work shows that one may expect significant improvement of lateral resolution (LR) using very simple NFT (e.g., metal nanoparticle attached to AFM probe). One should also expect improvement in signal-to-noise ratio of TE spectroscopy since noise in this case is collected from the much reduced sample area (the same signal but about 100 reduced noise compared to SIL about 200 nm and TE about 20 nm cases).

In these simulations the object of interest is placed right under the NFT in nanometer proximity. Such experimental setup can be difficult to realize in case of optical circuit analysis, where IC should be powered from the top and photon collection should be done from the backside or in another embodiment electrical probes deliver power to the circuit from the frontside and emitted photon will be also collected at the frontside. In both cases photons will travel through and scatter by crystalline silicon (c-Si) or thin films of silicon dioxide (pre-metal dielectric). This may cause reduction in LR and photon collection efficiency. Recently backside c-Si polishing of functioning IC down to 70 nm remaining thickness has been demonstrated. Samples with 20 nm to 50 nm thick pre-metal dielectrics are used today in nanoprobing. Optimal NFT LR for those samples should be in the range of 30-50 nm. As it follows from data presented in FIG. 3, the LR of 30 nm can be achieved.

The next example demonstrates utilization of 80 nm silver particle to enhance fluorescence of dye molecules placed on glass surface, illustrated in FIGS. 4A and 4B. FIG. 4A illustrates the normalized fluorescence rate as a function of antenna-molecule separation. Dots are data, and the curve is the result of a theoretical calculation. The inset is a scanning electron microscope image of the nanoparticle antenna. The particle is held by a dielectric tip, the wavelength, $\lambda$=488 nm. FIG. 4B illustrates fluorescence rate image recorded by raster scanning of a sample with dispersed dye molecules in a plane z≈5 nm underneath a nanoparticle antenna. The different fluorescence patterns are due to different orientations of the molecular transition dipole axis.

The experiment confirms TE Raman Spectroscopy (TERS) sensitivity to a single molecule and also high spatial resolution of silver nanoparticle based imaging system. This data confirms the simulations. Importantly TERS shows noticeable enhancement only when the distance between NFT (Ag particle) and the sample (dye molecule) is less than 10 nm. For Z=50 nm no enhancement is observed. The same poor enhancement one should expect for imaging through 50 nm thick c-Si (backside) or pre-metal dielectric (frontside).

According to another example, a C-shaped aperture is integrated with a nano-tip (referred to herein as c-aperture nano tip, or CAN-tip) NFT. This NFT uses both a c-shaped aperture resonance and a tip antenna resonance, which can be tuned independently. Finite-difference time domain simulations predict that the CAN-Tip provides high intensity (650×), high optical resolution (~$\lambda$/60), and background-free near-field illumination at a wavelength of 980 nm. The near-field optical resolution of 16.1 nm has been experimentally confirmed by employing the CAN-Tip as an NSOM probe.

FIG. 5A is a schematic of the CAN-Tip, while FIG. 5B is a plot of the near-field profile as calculated for 980 nm light at 6 nm from the tip of a CAN-Tip. The FWHM near-field spot size is 18.36 nm×18.36 nm. The grey-level bar shows the normalized intensities. White lines delineate relative positions of the aperture in each figure. The characteristic sizes of the C-aperture is 40 nm and the radii of curvature at the tip is 10 nm.

FIGS. 6A and 6B compare transmission and peak light intensity of C-aperture with characteristic size a =100 nm and square aperture of 100 nm size. Both structures have comparable spot sizes. The comparison is for 980 nm light. Both structures have comparable lateral resolution. Spot size is 128 nm×136 nm and 140 nm×80 nm for C-aperture and square aperture, respectively. The C-aperture has 600× higher power throughput and 2000× higher peak light intensity. The C-aperture and the square aperture have transmissions of 88% and 0.2%, respectively. Combining this C-aperture with tip creates new NFT with very high transmission (defined by the aperture dimensions) and lateral resolution (defined by probe apex diameter). The CAN-tip is a new and very promising type of NFT. This NFT, as all tip based transducers, is also design to operate in close proximity (~10 nm) to sample.

Integration of NFT in Photon Delivery and Photon Collection Schemes

Figure 8:
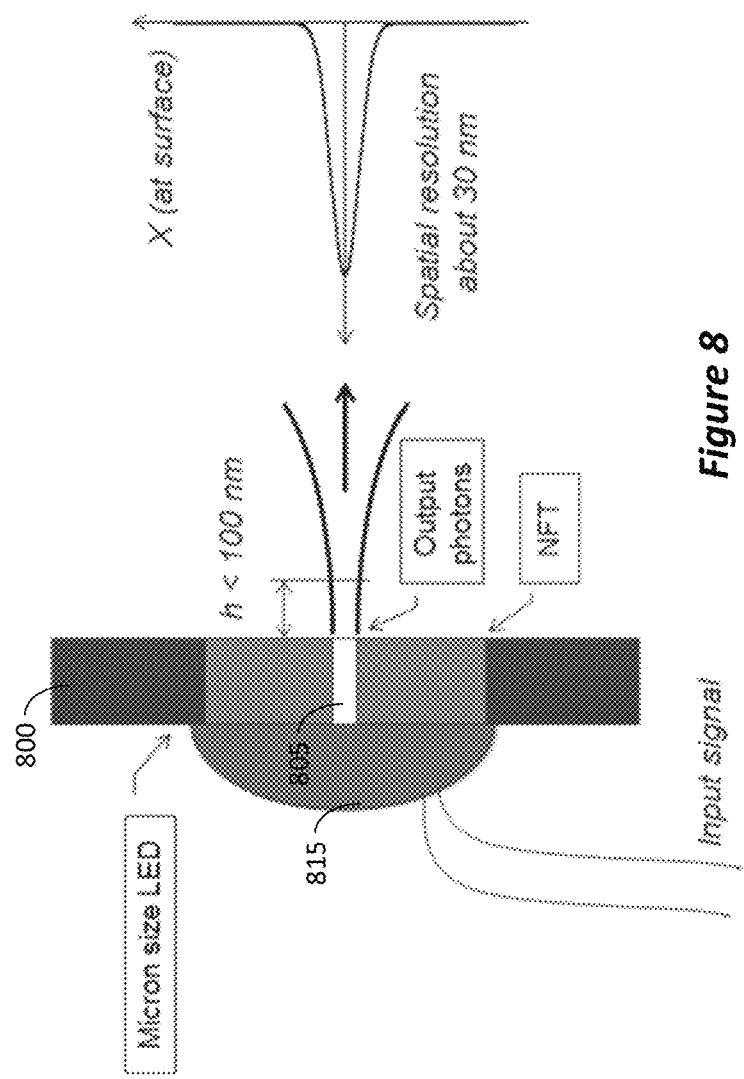
FIG. 8 illustrates integration of NFT and source of photons, according to one embodiment.

FIGS. 7 and 8 show examples of NFT integration schemes used for high-resolution photon collection (FIG. 7) and photon delivery (FIG. 8). In both cases NFT is used for high transmission focusing of photons below diffraction limit. Expected wavelength of photons emitted by p/n junction is in the range from 1000 nm to 2000 nm at low Vdd operating voltages of mobile devices, when the silicon is not so thin. When the silicon is real thin then shorter wavelength photons can be captured. But always there are more of the longer wavelength photons. Therefore, photon collection efficiency of NFT used in collection scheme (FIG. 7) should be optimized around 1500 nm. Ideally, NFT should have depth of focus up to 100 nm and NFT transmission should be optimized at depth of 50 nm or so. Thicker films between NFT and sample degrade the spatial resolution. Shorter focus depth of NFT provides better spatial resolution and higher transmission in general. The fact that the thickness of active silicon reduces with process node tends to scale the necessary resolution with the remaining silicon thickness which enables the IC to operate. Coupling of photon sensor and NFT can be done in various ways including direct attachment of sensor to NFT (FIG. 7), using optical fiber or/and simple optics (lens).

The embodiment of FIG. 7, demonstrates an integration of NFT and photosensor in photon collection scheme. The NFT 700 has a nano-scale aperture 705, having a diameter that is much smaller than the wavelength of collected photons. The aperture may have various shapes, e.g., circular, bowtie, c-shape, etc. The NFT 700 is configured for placement at a distance h from the sample, wherein h is much smaller than the wavelength of the collected photons. The sensor 710 may be, e.g., nanoelectromechanical systems or NEMS built nanoscale thermocouple or thermal resistor. The photosensor 710 is attached to the NFT 700 directly behind the aperture 705. This scheme promises tens of percent photon collection efficiency with spatial resolution of about 30×30 nm$^2$.

FIG. 8 illustrates integration of NFT 800 and source of photons 815 in photon delivery scheme. The photon source 815 may be, for example, a micron size LED with wavelength above 1000 nm. As an option, optical fiber or simple optics (focusing lens) can be inserted between LED and NFT. High transmission light focusing below diffraction limit is provided by NFT.

Coupling of LED 815 and NFT 800 can be done in various ways, including direct attachment of LED 815 to the NFT 800, using optical fiber or/and simple optics (lens). Remote location of the LED 815 (option of optical fiber) may be beneficial since this will reduce thermal impact of the LED on nanopositioners and the sample. Reduction of thermal system drift can be critical for some applications. Photon energy of the LED should be optimized depending on the application. In most cases wavelength below about 1060 nm (size of energy gap of c-Si) should be adequate for delivery photo energy to the elements of IC. Absorption of photons in 50 nm thick c-Si layer (backside probing) should be high enough to provide local heating or photo excitation of the elements of IC. Use of pulsing and lock-in amplifying should improve signal-to-noise ratio of probing.

FIG. 9 shows an embodiment of integration of NFT 900 with single-mode optical fiber 920. The CAN-tip 925 is a good combination of two different NFT's which provides optimization for the specific wavelength transmission and also delivers controllable (defined by the size of tip apex) spatial resolution. The diameter of commercially available single mode optical fiber is in the range of from 8 μm to 10.5 μm. Even the 8 μm diameter fiber will block significant area of the IC, complicating navigation of optical probe (NFT) to the ROI. Therefore, additional narrowing of the fiber to sub-wavelength diameter is strongly recommended, as illustrated by tapper section 930 in FIG. 9. In this respect, a single-mode optical fiber (SMF) is an optical fiber designed to carry light only directly down the fiber, also referred to as the transverse mode since its electromagnetic vibrations occur perpendicular (transverse) to the length of the fiber.

To fabricate the apparatus of the embodiment of FIG. 9, a single mode fiber 920 is thinned (930) to sub-wavelength diameter 935. In the example of FIG. 9 the tip is configured for wavelength of 1060 nm, so the tip of the fiber is thinned to a diameter below the wavelength, in this example 700 nm. The thinned bottom end of the fiber is then covered with about 150 nm thick film of metallic layer coating 940, e.g., gold or silver layer. FIB is used to cut C-aperture 945 in the gold layer 940, with dimensions optimized for specific wavelength. Then metal tip 950 of about 50 to 100 nm height is grown in the center of the C-aperture using FIB assisted chemical vapor deposition (CVD) process. FIB is also used to sharpen the tip apex 955 to diameter of 20 to 30 nm. FIB assisted CVD is then used to grow 20 to 30 nm metal alignment marks 955 on the outer perimeter of the fiber. The FIB can also be used to etch, instead of grow, alignment marks. These marks are visible with top-down SEM and may be used to simplify optical probe navigation to the ROI. The marks may alternatively be deposited with an ebeam.

FIGS. 9A-9E illustrate various embodiments for apertures made through the metallic layer coating 940 at the tip of the fiber. FIG. 9A illustrates a circular hole surrounded by concentric grooves, FIG. 9B illustrates the C-aperture of the embodiment of FIG. 9, FIG. 9C illustrates a triangle aperture, FIG. 9D illustrates an L-shaped aperture, and FIG. 9E illustrates a bowtie aperture. As can be seen from FIGS. 9A-9E, the C-shaped aperture is most fit for use with the metal tip 950.

Figure 10:
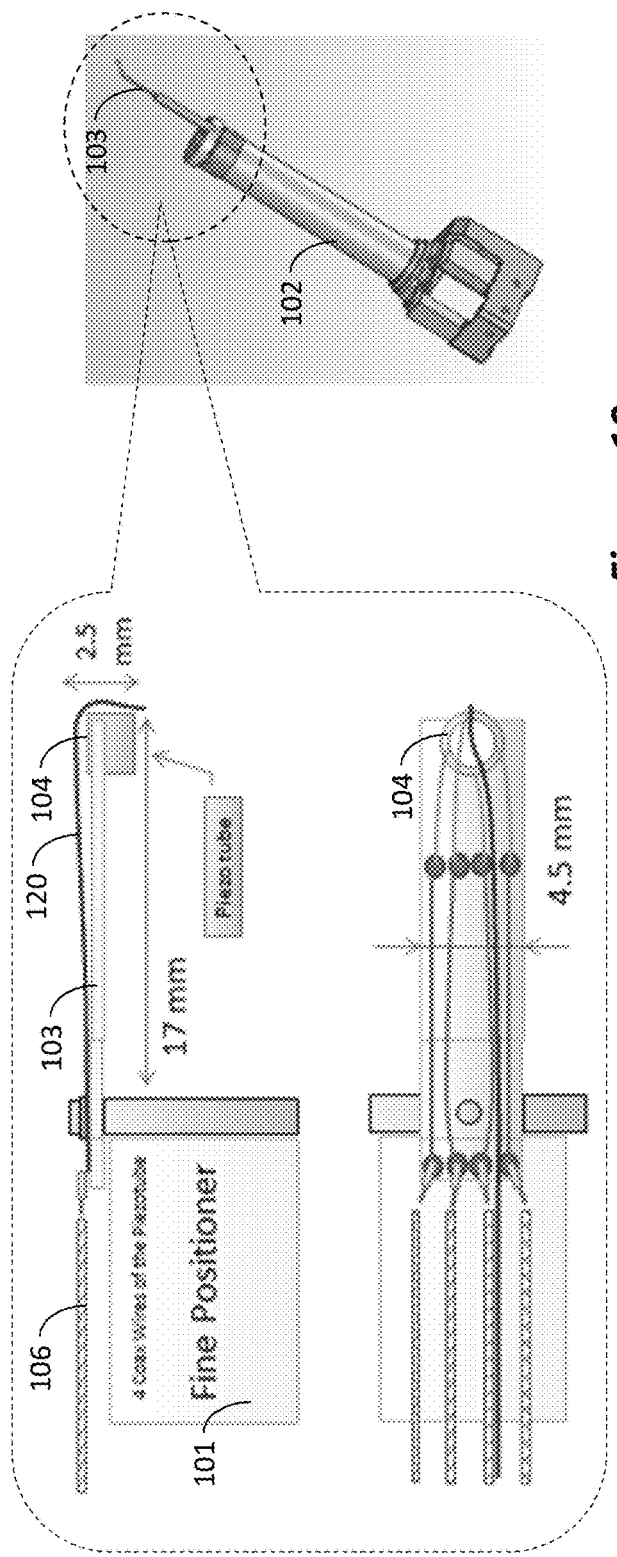
FIG. 10 is a schematic illustration of integration of optical fiber and NFT with probe positioner of modern nanoprobing system, according to one embodiment.

According to various embodiments disclosed herein, optical or/and scanning electron microscope are used to navigate the optical and electrical probes to the ROI. First, a sample stage motion is used to bring the ROI to the pre-set location, e.g., the origin of the system of the tool's coordinates. Then, when the ROI is positioned under the probe, scanning or stepping of optical near-field and electrical probes over the ROI is done using probe positioners, which are pre-registered with the system of the tool's coordinates. Prior to describing the integration of the NFT with the testing system, a description of the integration of the optical fiber NFT with a nanoprober is provided. FIG. 10 shows example of integration of optical fiber and NFT with probe positioner of modern nanoprobing system.

FIG. 10 is a schematic illustration of integration of optical fiber having an NFT at its tip with probe positioner of modern nanoprobing system, according to one embodiment. The drawing inside the callout of FIG. 10 illustrates the elements of this embodiment that are installed on a standard probe positioner 102. The elements inside the callout will be explained herein, while the elements of the standard probe positioner 102 need not be discussed, since any standard probe positioner may be used.

Referring to FIG. 10, a fine positioner 101 controls the fine movement of fork 103. An oscillating piezo tube 104 is affixed to the end of the fork 103 and is coupled to four coaxial wires 106. The oscillating piezo tube 104 is used to detect sample surface touch and/or proximity during probe landing on the sample. This is done through monitoring of the dampening of the probe's oscillations (amplitude and/or phase). An optical fiber 120, formed into a transducer according to any of the embodiments disclosed herein, is attached to the piezotube 104, so as to maintain a specified angle and/or the distance between the NFT at the tip of the fiber 120 (too small to be shown) and the sample's surface. According to one embodiment, the optical fiber 120 is glued to the piezotube 104. Generally during use the distance between the sample and the NFT at the tip of the fiber 120 varies between a few nm to 10 nm.

Figure 11:
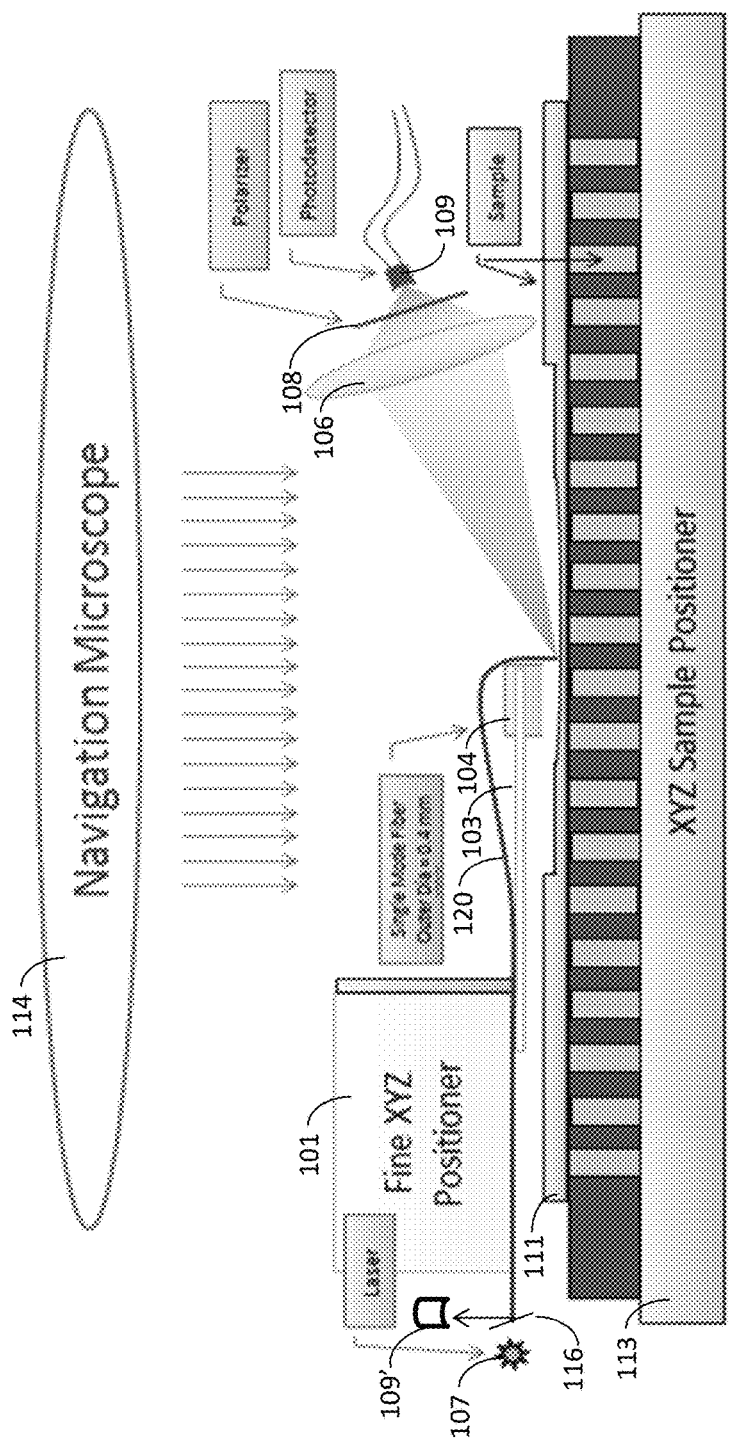
FIG. 11 illustrates a setup for backside optical nanoprobing of electrically active IC, according to a disclosed embodiment.
Figure 12:
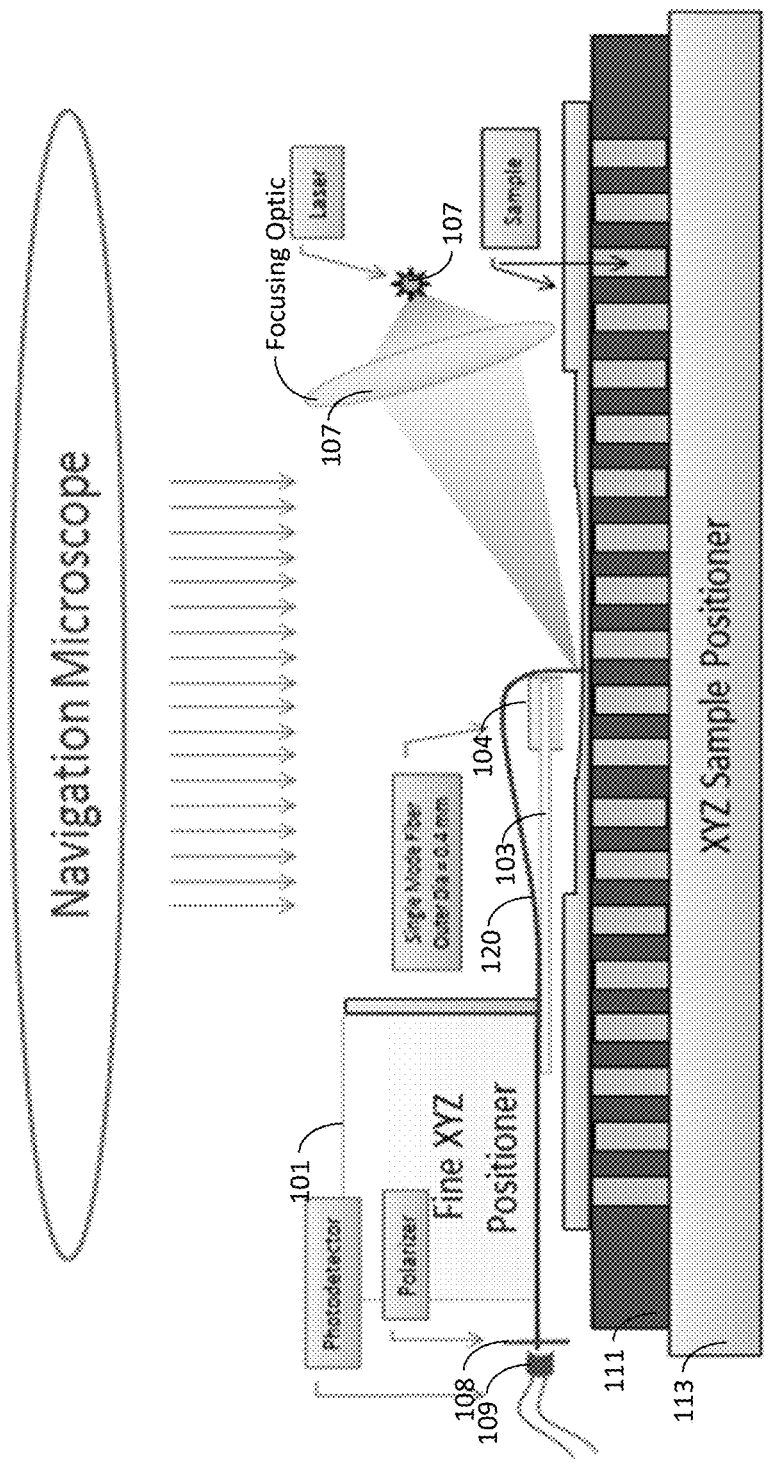
FIG. 12 illustrates a setup for backside optical nanoprobing of electrically active IC, according to a disclosed embodiment.
Figure 13:
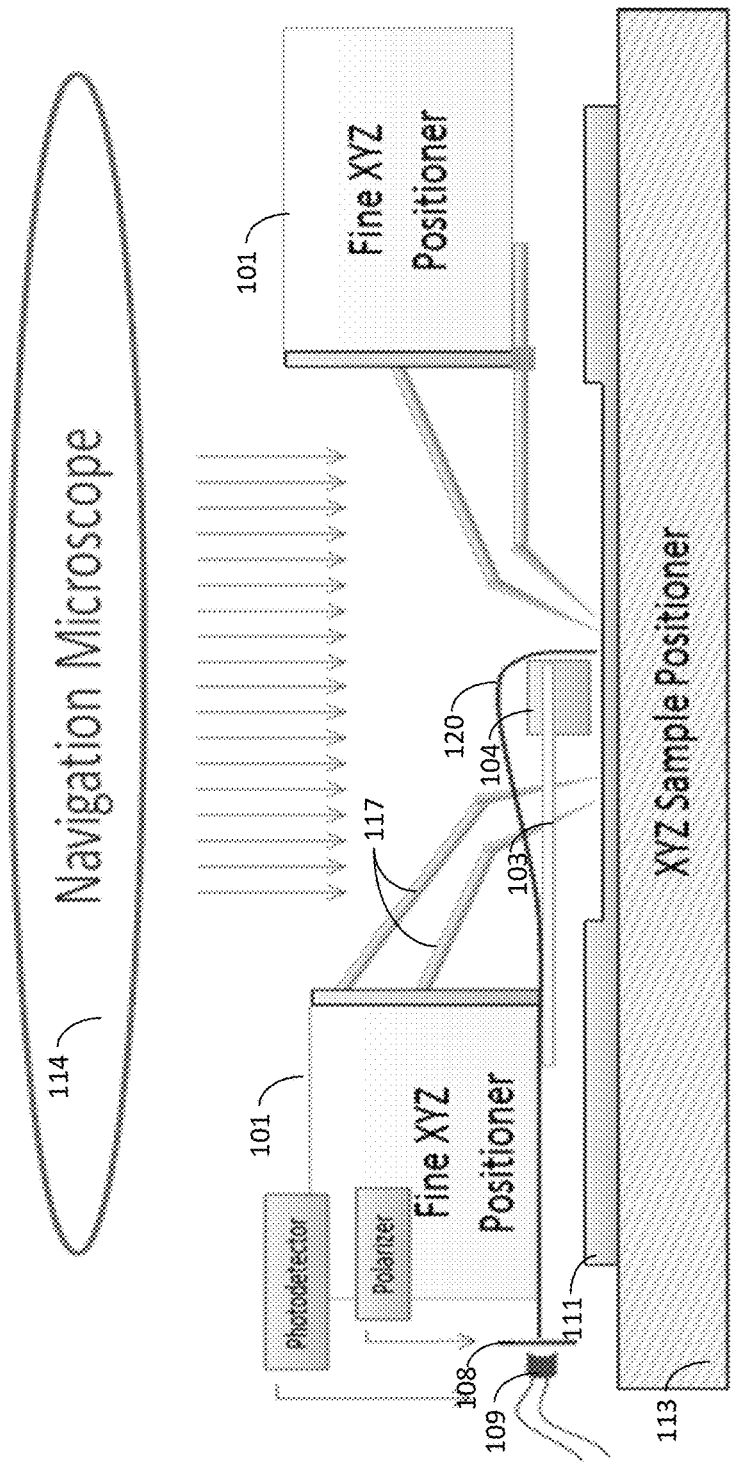
FIG. 13 illustrates a setup for frontside optical nanoprobing of electrically active IC, according to a disclosed embodiment.

Optical near-field probes according to any of the disclosed embodiments can be used in various setups. Near-field sensors can be used for photon delivery to the sample (FIGS. 11, 14), and photon collection from the ROI of the sample (FIGS. 12, 13). Far-field optics can be used in combination with near-field optics (FIGS. 11, 12). Optical probes can be used with wafer electrical testers (FIGS. 11, 12) for backside OCA or/and together with electrical nanoprobes (FIGS. 13, 14) for frontside OCA. Some of these arrangements will be demonstrated in the following embodiments.

FIG. 11 illustrates a setup for backside optical nanoprobing of electrically active IC. The embodiment illustrated in FIG. 11 can be used in static laser stimulation (SLS) and dynamic laser stimulation (DLS) schemes of optical circuit analysis. The sample 111 (in this example a thinned integrated circuit chip) is placed on a sample positioner 113. The sample positioner 113 may be an x-y-z stage, in which case the x-y-z-stage can be used to register the sample to the system's coordinates for easy navigation to the region of interest (ROI). A navigation microscope 114 may then be used to place the ROI under, or within the scanning reach of the nanoprober positioner 101. The navigation microscope may be photon, electron, or ion microscope. Electron microscope may provide beneficial accuracy, but may involve higher cost due to vacuum requirements.

The nanoprobe positioner then places the NFT formed at the tip of the optical fiber 120 to a prescribed distance from top surface of the ROI, wherein the prescribed distance comprises near-field proximity, near-field proximity being a fraction, e.g., one-tenth, of the wavelength used during the probing. In the example of FIG. 11, the wavelength is the wavelength of the laser source 107. In order to accurately place the NFT at the near-field proximity to the top surface of the ROI, the dampening of the piezo tube 104 is monitored. The dampening may be monitored by sensing the amplitude, phase or amplitude and phase of the oscillations of the piezo tube 104, coupled to the fork 103.

For certain probing, the sample 113 may be energized with test signals, sometimes referred to as test vectors, applied by, for example, conventional automated testing equipment (ATE), which is not shown in this illustration. ATE's are well known and are used to send test vectors into the IC and sense the electrical response to the IC to the test vectors.

In the embodiment of FIG. 11, while the test vectors are applied to the IC, a laser 107 generates a laser beam, which is coupled into the optical fiber 120. The NFT at the exit tip of the optical fiber is used to deliver the photons from the laser beam to the ROI. Since the laser beam traverses the optical fiber in a single mode and exits the tip via the NFT, the photons are focused into a very small spatial distribution over the ROI. That is, photon delivery can be to a nano-scale accuracy so as to target a specific device or specific node within the IC. Scattered light is then collected using far-field optics 106 and is directed towards the photodetector 109. In this embodiment, a polarizer 108 is used to enhance the signal-to-noise ratio. Additionally, the optical fiber may be used to both deliver the laser beam to the ROI and collect reflected photons from the ROI. For example, the laser beam may be pulsed, such that after the pulse is delivered to the ROI, the optical fiber can be used to collect reflected photons. For such an embodiment, optional deflection optics 116, e.g., half mirror, can be used to deflect collected photons onto photodetector 109'.

FIG. 12 illustrates a setup for backside optical nanoprobing of electrically active IC. Many of the elements of FIG. 12 are similar to those shown in FIG. 11, and are therefore indicated by the same reference characters. In this embodiment, the far-field focusing optics 106 is used to focus a laser beam from laser source 107 onto the ROI. The NFT at the tip of the single mode fiber 120 collects the photons reflected or scattered from a spatial area defined by the collection resolution of the NFT. In this embodiment, the illumination and collection may be performed while the depackaged and thinned sample 111 is electrically activated using a tester, such as an ATE. In one example, the far-field optics 106 is used to deliver polarized laser beam to the ROI. A polarizer 108, positioned at the end of the fiber 120, may be used to enhance the signal-to-noise ratio. As in the example for FIG. 11, this setup can be used in SLS and DLS schemes of OCA.

In an alternative embodiment, photodetector 109 is a superconducting nanowire single-photon detectors (SNSPD). Such an embodiment may be used to detect single photons emitted from active devices within the IC, without illumination from laser 107. For an efficient SNSPD emission detection, a lens may be placed at the position of the polarizer 108, i.e., between the exit tip of the fiber optics 120 and the photodetector 109. Using this setup, the system forms an emission microscope with the ability to resolve the emission to nano-scale spatial resolution. Moreover, by synchronizing the signal of the SNSPD to the clock of the ATE, the system can form a time resolved emission microscope with the ability to resolve the emission to nano-scale spatial resolution. In either case, the system is able to resolve emissions with higher resolution than is possible today with a solid immersion lens (SIL).

FIG. 13 illustrates a setup for frontside optical nanoprobing of electrically active IC. Many of the elements of FIG. 13 are similar to those shown in FIG. 11, and are therefore indicated by the same reference characters. In this embodiment, NFT formed at the tip of the fiber 120 is used for collection of photons emitted by the devices of the depackaged and delayered IC 111. The IC 111 is electrically activated using nanoprobes 117 (4 probes are shown). The nanoprobes 117 are conductive nanoprobes that are actuated by the positioner 101 to be accurately placed on selected conductive elements within the ROI. The nanoprobes 117 can be used to deliver test vectors directly to the selected conductive elements within the ROI. When the test vectors cause transistors to switch state, the transistors emit photons. Photons emitted within the collection radius of the NFT are transmitted through the fiber 120 towards the exit tip of the fiber 120. A polarizer 108 may be placed at the exit tip of the fiber 120 and is used to enhance the signal-to-noise ratio. The photons are then detected by photodetector 109. This setup can be used in static and dynamic stimulation schemes of OCA.

Figure 14:
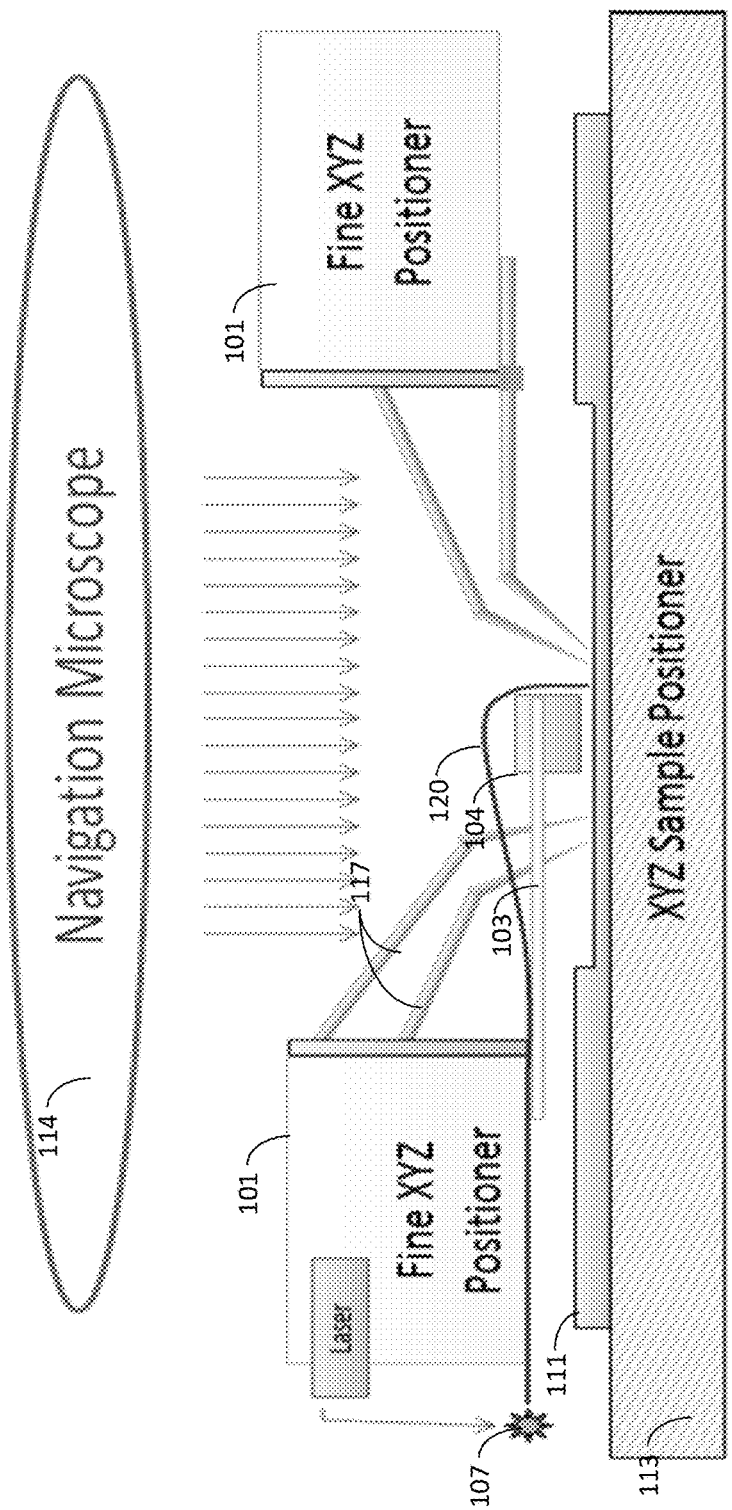
FIG. 14 illustrates a setup for frontside optical nanoprobing of electrically active IC, according to a disclosed embodiment.

FIG. 14 illustrates a setup for frontside optical nanoprobing of electrically active IC. Many of the elements of FIG. 14 are similar to those shown in FIG. 13, and are therefore indicated by the same reference characters. In this embodiment, NFT at the tip of optical fiber 120 is used for photon delivery to the devices of the depackaged and delayered IC 111. The IC 111 is electrically activated using nanoprobes 117 (4 probes are shown). This setup can be used in SLS and DLS schemes of OCA. For example, test signals may be applied to the IC via the nanoprobes 117, and the electrical response of various devices within the IC can be detected using the nanoprobes 117. Then, laser source 107 is activated and a laser beam is coupled into the fiber optic 120 so as to focus the beam onto a specific location within the ROI, thereby heating that location. The test signals are then applied again to the IC via the nanoprobes 117, and the electrical response of various devices within the IC under the heating condition are detected using the nanoprobes 117. This can be used to detect devices that are subject to failure under certain operating conditions.

The foregoing description, for purpose of explanation, has been described with reference to specific embodiments. However, the illustrative discussions above are not intended to be exhaustive or to be limiting to the precise forms disclosed. Many modifications and variations are possible in view of the above teachings. The embodiments were chosen and described in order to best explain the principles of the aspects and its practical applications, to thereby enable others skilled in the art to best utilize the aspects and various embodiments with various modifications as are suited to the particular use contemplated.

The invention claimed is:

1. A prober integrating a near-field transducer, comprising:
   a probe spatial positioner;
   a fork attached to the positioner;
   an oscillating piezotube attached to a free end of the fork;
   electrical leads attached to the oscillating piezotube;
   an optical fiber having a near-field transducer formed at an end thereof, the optical fiber being attached to the oscillating piezotube such that the near-field transducer extends below the oscillating piezotube;
   wherein the near-field transducer comprises a tapered section formed at the end of the optical fiber, a metallic coating formed at a tip of the tapered section, and an aperture formed in the metallic coating so as to expose the tip of the tapered section through the metallic coating.

2. The prober of claim 1, wherein the near-field transducer further comprises a metal tip extending from the metallic coating.

3. The prober of claim 2, wherein the metal tip extends to a height of from 50 nm to 100 nm and has a tip apex of diameter of from 20 nm to 30 nm.

4. The prober of claim 2, wherein the aperture has a C shape, and the metal tip is formed at central part of the c-shape aperture.

5. The prober of claim 1, wherein the metallic coating comprises a gold layer.

6. The prober of claim 1, further comprising alignment marks provided on the metallic coating.

7. The prober of claim 6, wherein the alignment marks comprise metallic bumps.

8. The prober of claim 6, wherein the alignment marks comprise etched marks.

9. The prober of claim 1, wherein the tip of the tapered section has a diameter smaller than wavelength of photons to be detected.

10. A method for fabricating a near-field transducer for operating at preselected wavelengths, comprising:
    providing a single mode fiber having a diameter larger than the wavelengths;
    forming a thinned section at one end of the single mode fiber, wherein the thinned section terminates at a flat bottom having a diameter that is smaller than the wavelengths;
    coating the flat bottom with an opaque layer;
    cutting an aperture in the opaque layer, the aperture having dimensions optimized for the preselected wavelengths and being smaller than the preselected wavelengths;
    growing a metal tip on the opaque layer in the vicinity of the aperture; and,
    forming alignment marks on an outer perimeter of the opaque layer.

11. The method of claim 10, wherein the opaque layer is made of gold.

12. The method of claim 10, wherein the aperture is formed to have a C shape.

13. The method of claim 12, wherein the metal tip is formed at the center of the C shape aperture.

14. The method of claim 10, wherein the tip is grown to have a height of from 50 to 100 nm.

15. The method of claim 10, wherein the tip is grown using focus ion beam assisted chemical vapor deposition.

16. The method of claim 10, wherein the alignment marks are metallic bumps grown using focused ion beam.

17. The method of claim 10, wherein the alignment marks are etched onto the opaque layer using focused ion beam.

18. An apparatus for performing electrical and optical sample nanoprobing with resolution beyond optical diffraction limit, comprising:
    a sample holder;
    a navigation microscope configured for navigation over the sample to a region of interest (ROI);
    a probe spatial positioner;
    a fork attached to the positioner;
    an oscillating piezotube attached to a free end of the fork and providing an output indicating of a distance to the sample;
    electrical leads attached to the oscillating piezotube;
    a single-mode optical fiber having a near-field transducer formed at an end thereof, the optical fiber being attached to the oscillating piezotube such that the near-field transducer extends below the oscillating piezotube towards the sample;
    a photodetector;
    wherein the near-field transducer comprises a tapered section formed at the end of the single-mode optical fiber, a metallic coating formed at a tip of the tapered section, and an aperture formed in the metallic coating so as to expose the tip of the tapered section through the metallic coating.

19. The apparatus of claim 18, further comprising:
    a laser positioned to provide a laser beam into the single-mode optical fiber;
    a collection objective positioned to collect light reflected from the sample and direct the reflected light onto the photodetector;
    a polarizer positioned between the collecting objective and the photodetector.

20. The apparatus of claim 18, further comprising:
    a laser positioned to provide a laser beam towards the sample;
    an objective positioned to focus the laser beam from the laser source onto the ROI;
    a polarizer positioned at an exit side of the single-mode optical fiber;
    wherein the photodetector is positioned behind the polarizer and receives light passing through the polarizer.

21. The apparatus of claim 18, further comprising a plurality of conductive nanoprobes attached to the positioner and electrically coupled to a signal source.

22. The apparatus of claim 21, further comprising a polarizer positioned at an exit side of the single-mode optical fiber; and wherein the photodetector is positioned behind the polarizer and receives light passing through the polarizer.

23. The apparatus of claim 21, further comprising a laser positioned to provide a laser beam into the single-mode optical fiber.

24. A method of probing a sample in a probing system using a near-field transducer (NFT) integrated with a nanoprober, comprising:
    affixing a sample to a stage;
    affixing a single mode fiber optic, having an NFT formed at its sampling tip, to a piezo tube, wherein the piezo tube is attached to a fork of a nanoprober;
    using the stage to register a region of interest (ROI) of the sample to coordinates of the probing system;
    energizing a positioner of the nanoprober to bring NFT to within a prescribed distance from top surface of the ROI, wherein the prescribed comprises near-field proximity;
    determining proximity of the NFT to the top surface by monitoring of dampening of piezo tube;
    scanning the NFT over the top surface of the ROI.

25. The method of claim 24, wherein monitoring of dampening of piezo tube comprises monitoring amplitude, phase or amplitude and phase of oscillations of the piezo tube.

26. The method of claim 24, further comprising illuminating the ROI with a laser beam.

27. The method of claim 26, wherein illuminating the ROI with a laser beam comprises directing the laser beam into the single mode fiber optic.

28. The method of claim 26, wherein illuminating the ROI with a laser beam comprises directing the laser beam onto the ROI using a focusing optics.

29. The method of claim 28, further comprising using a photodetector to detect photons collected from the sample by the single mode fiber optic.

30. The method of claim 29, further comprising placing a polarizer between the photodetector and an exit end of the single mode fiber optic.

31. The method of claim 24, further comprising contacting the sample with a plurality of conductive nanoprobe tips and applying test signals to the sample via the nanoprobe tips.

32. The method of claim 31, further comprising using a photodetector to detect photons collected from the sample by the single mode fiber optic while applying the test signals.

33. The method of claim 31, further comprising using directing the laser beam into the single mode fiber optic while applying the test signals, and using the nanoprobe tips to collect electrical signals from the ROI in response to applying the test signals and the laser beam.

* * * * *